(12) United States Patent
Camenisch et al.

(10) Patent No.: US 7,709,532 B2
(45) Date of Patent: May 4, 2010

(54) METHODS FOR IMPROVING BIOAVAILABILITY OF A RENIN INHIBITOR

(75) Inventors: Gian P. Camenisch, Riehen (CH); Gerhard Gross, Lörrach (DE); Isabel Ottinger, Freiburg (DE); Daniel Wasmuth, Bättwil-Flüh (CH)

(73) Assignee: Novartis AG, Basel (CH)

( * ) Notice: Subject to any disclaimer, the term of this patent is extended or adjusted under 35 U.S.C. 154(b) by 313 days.

(21) Appl. No.: 11/572,471

(22) PCT Filed: Aug. 2, 2005

(86) PCT No.: PCT/EP2005/008369

§ 371 (c)(1), (2), (4) Date: Apr. 17, 2007

(87) PCT Pub. No.: WO2006/013094

PCT Pub. Date: Feb. 9, 2006

(65) Prior Publication Data

US 2008/0108703 A1 May 8, 2008

Related U.S. Application Data

(60) Provisional application No. 60/598,700, filed on Aug. 3, 2004.

(51) Int. Cl.
*A61K 31/165* (2006.01)
*A61P 9/00* (2006.01)

(52) U.S. Cl. .................................................... 514/616

(58) Field of Classification Search ........................ None
See application file for complete search history.

(56) References Cited

U.S. PATENT DOCUMENTS

| | | | | |
|---|---|---|---|---|
| 6,028,054 A | | 2/2000 | Benet et al. ..................... | 514/9 |
| 6,121,234 A | | 9/2000 | Benet et al. ..................... | 514/11 |
| 6,869,970 B2 | * | 3/2005 | Marti .............................. | 514/381 |
| 7,115,565 B2 | * | 10/2006 | Gao et al. ....................... | 514/9 |
| 2002/0127669 A1 | | 9/2002 | Knipp et al. .................... | 435/183 |
| 2004/0137054 A1 | * | 7/2004 | Hager et al. .................... | 424/465 |

FOREIGN PATENT DOCUMENTS

| | | |
|---|---|---|
| EP | 0 614 976 | 9/1994 |
| EP | 0742 722 | 4/2002 |
| WO | WO 96/40192 | 12/1996 |
| WO | WO 03/053401 | 7/2003 |
| WO | WO 2004/002466 | 1/2004 |
| WO | WO 2005/089731 A | 9/2005 |

OTHER PUBLICATIONS

Reily et al., "Design, Synthesis and Solution Strucutre of a Renin Inhibitor", FEBS, 1992, vol. 302, No. 1, pp. 97-103.*
Weber et al., "Design and Synthesis of P2.P1'-Linked Macrocylic Human Renin Inhibitors", J. Med. Chem., 1991, vol. 34, pp. 2692-2701.*
Avdonin et al., "Cyclosporine A Up-Regulates Angiotensin II Receptors and Calcium Responses in Human Vascular Smooth Muscle Cells", Kidney International, vol. 55, 1999, pp. 2407-2414.*
Mital et al., "Simvastatin Acts Synergistically with ACE inhibitors or Amiodipine to Decrease Oxygen Consumption in Rat Hearts", Journal of Cardiovascular Pharmacology, abstract, 2000, vol. 36, No. 1, pp. 248-254.*
Muller et al., "Cardiovascular Drus and Therapy", 1998, vol. 12, pp. 449-455.*
Chen et al., Drug Metabolism and Disposition, vol. 33, No. 4, pp. 537-546.*
Bittner et al., Arzneimitte- Forschung/Drug Res. 52, No. 8, pp. 593-599 "Performulation approaches to Improve the Oral Bioavailability of Two Novel Piperidine Renin Inhibitors in Dog" (2002).
Kunta et al., Current Drug Metabolism, vol. 5, pp. 109-124, "Intestinal drug transporters: in vivo function and clinical importance" (2004).
Takahashi et al., FASEB Journal Abstracts, vol. 9, No. 3, p. A308 (1995).
Takahashi et al., The Journal of Pharmacology and Experimental Therapeutics, vol. 281, No. 1, pp. 297-303, "Characterization of the hepatic canalicular membrane transport of a model oligopeptide: Ditekiren¹", (1997).
Tsuji et al., Pharmaceutical Research, vol. 13, No. 7, pp. 963-977 "Carrier-mediated intestinal transport of drugs" 1996).
Ziegler et al., Biochimica et Biophysica Acta 1196, pp. 209-217, "ATP-dependent transport of the linear renin-inhibiting peptide EMD 51921 by canalicular plasma membrane vesicles of rat liver: evidence of drug-stimulatable ATP-hydrolysis", (1994).

* cited by examiner

*Primary Examiner*—Brian-Yong S Kwon
(74) *Attorney, Agent, or Firm*—Lisa M. Matovcik; Gregory D. Ferraro (57) ABSTRACT

The present invention provides a method for improving the bioavailability of a renin inhibitor, preferably, of a δ-amino-γ-hydroxy-ω-aryl-alkanoic acid derivative, which method comprises co-administering to a mammal, especially a human, in need of such treatment, a combination of a renin inhibitor, or a pharmaceutically acceptable salt thereof, and an efflux protein inhibitor.

6 Claims, 5 Drawing Sheets

METHODS FOR IMPROVING BIOAVAILABILITY OF A RENIN INHIBITOR

This application claims benefit of U.S. Provisional Application No. 60/598,700, filed on Aug. 3, 2004.

The oral route is often the most convenient route for drug administration, but unfortunately many therapeutic agents are not orally active due to their poor bioavailability.

The bioavailability of many therapeutic agents may be reduced by the action of so-called "efflux pump" proteins which actively eject foreign substances from the cell to give rise, for example, to the multidrug resistance effect. These drug efflux proteins principally comprise MDR (multidrug resistance protein) and MRP (multidrug resistance associated protein) type transporters. Some of the best studied efflux proteins include P-glycoprotein (Pgp or MDR1) and MRP2.

Although membrane located efflux proteins are well known as a factors contributing to the acquired multidrug resistance syndrome arising in many cancer patients after repeated chemotherapy, it has only recently been realized that, e.g., MDR1, is also found in the normal tissue such as small intestine, colon, liver and endothelial cells in the blood brain barrier. The presence of such efflux proteins in the gastrointestinal (GI) tract, especially, in the small intestine and colon, may contribute to the poor bioavailability of many natural product drugs (including the anticancer agents vinblastine and doxorubicin). For example, many chemotherapeutic agents given orally can not show anti-tumor activity due to poor bioavailability and their inability to enter GI tissues. Furthermore, efflux proteins present in hepatocytes may additionally reduce the bioavailability of therapeutic agents by elimination via bile (see Faber et al., *Adv. Drug Del. Rev.*, 55, 107-124, 2003).

Orally administered therapeutic agents must overcome several barriers before reaching their target site. The first major obstacle to cross is the intestinal epithelium. Although lipophilic compounds may readily diffuse across the apical plasma membrane, their subsequent passage across the basolateral membrane and into portal blood is by no means guaranteed. Efflux pump proteins located at the apical membrane, which include various drug transporters of the ATP-binding cassette (ABC) family, e.g., ABC transporters such as MDR1, MRP1 and MRP2, may drive compounds from inside the cell back into the intestinal lumen, restricting their oral bioavailability by preventing their absorption into blood. The second major hurdle to face is the liver where drugs are transported passively or by saturable transport processes from the portal blood across hepatocyte plasma (sinusoidal) membranes and bile (canalicular) membranes into bile. Efflux pump proteins located at the canalicular membranes, which again include various drug transporters of the ABC family, e.g., ABC transporters such as MDR1, breast cancer resistance protein (BCRP) and MRP2, may drive drug compounds from inside hepatocytes into the bile, restricting their oral bioavailability by promoting biliary elimination. For example, MDR1 has been demonstrated to transport most HIV protease inhibitors and to reduce their oral bioavailability and lymphocyte, brain, testis and fetal penetration, possibly resulting in major limiting effects on the therapeutic efficacy of these drugs.

Therefore, one approach to improve bioavailability may be to co-administer an efflux protein inhibitor, i.e., a compound that inhibits the function of efflux proteins, with a drug substance. In other words, when an efflux protein inhibitor is co-administered with a therapeutic agent which is also a substrate for that specific efflux system, the oral bioavailability and/or the pharmacological active concentrations at the target site of the therapeutic agent may be enhanced by inhibiting the efflux mechanism from inside the cell back into the intestinal lumen and/or by inhibiting secretion into bile.

However, efflux proteins exhibit low substrate specificity, and transport many kinds of molecules. The specificity is not rigorously understood, and there is no way of predicting from the molecular structure of a drug substance whether that specific drug will be a substrate for a certain transporter protein. Thus, it is generally not possible to predict whether a particular drug or compound will be subject to the efflux pumping action discussed above. Also, if a particular drug has a low oral bioavailability, it is generally not possible to predict whether the low bioavailability is caused, wholly or partially, by the efflux proteins discussed above, nor can it be predicted whether the low bioavailability can be increased by co-administration of an efflux protein inhibitor (see Chan et al. *Eur. J. Pharmaceut. Sci.*, 21, 25-51, 2004).

Surprisingly, it has now been found that many renin inhibitors, e.g., those disclosed in U.S. Pat. No. 5,559,111, No. 6,197,959 and No. 6,376,672, the entire contents of which are incorporated herein by reference, are substrates for a prominent efflux system, and are actively transported by the members of the ABC family, in particular MDR1 and MRP2. Thus, the bioavailability of these renin inhibitors may be improved by inhibiting the efflux mechanism involved, in particular, by inhibiting the drug transport by MDR1 and/or MRP2.

The renin inhibitors to which the present invention applies are any of those having renin inhibitory activity in vivo and, therefore, pharmaceutical utility, e.g., as therapeutic agents for the treatment of hypertension, congestive heart failure, cardiac hypertrophy, cardiac fibrosis, cardiomyopathy postinfarction, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, anxiety states and cognitive disorders. In particular, the present invention relates to δ-amino-γ-hydroxy-ω-aryl-alkanoic acid amide derivatives as disclosed in U.S. Pat. No. 5,559,111.

Accordingly, the present invention provides a method for improving the bioavailability, preferably, oral bioavailability, of a renin inhibitor, which method comprises co-administering to a mammal, especially a human, in need of such treatment, a combination of a renin inhibitor and an efflux protein inhibitor. The efflux protein inhibitor is administered in an amount such that the bioavailability of a renin inhibitor is improved in comparison with what the bioavailability would be in the absence of the efflux protein inhibitor (e.g. 10% when administered orally to humans). An efflux protein inhibitor and a renin inhibitor are preferably each co-administered in an amount such that the combination has a desired therapeutic effect, e.g., an anti-hypertensive effect.

In particular, the present invention provides a method for improving the bioavailability of a δ-amino-γ-hydroxy-ω-aryl-alkanoic acid derivative, which method comprises co-administering to a mammal, especially a human, in need of such treatment, a combination of a δ-amino-γ-hydroxy-ω-aryl-alkanoic acid derivative, or a pharmaceutically acceptable salt thereof, and an efflux protein inhibitor.

The term "co-administration" of a combination of a renin inhibitor, in particular, a δ-amino-γ-hydroxy-ω-aryl-alkanoic acid derivative, and an efflux protein inhibitor means that the two components can be administered together as a pharmaceutical composition or as part of the same, unitary dosage form. Co-administration also includes administering a renin inhibitor, in particular, a δ-amino-γ-hydroxy-ω-aryl-alkanoic acid derivative, and an efflux protein inhibitor separately but as part of the same therapeutic regimen. The two components, if administered separately, need not necessarily be administered at essentially the same time, although they can if so desired. Thus, co-administration includes, for example, administering a renin inhibitor, in particular, a δ-amino-γ-hydroxy-ω-aryl-alkanoic acid derivative, plus an efflux protein inhibitor as separate dosages or dosage forms, but at the same time. Co-administration also includes separate administration at different times and in any order.

A renin inhibitor, in particular, a δ-amino-γ-hydroxy-ω-aryl-alkanoic acid derivative, of the present invention may be employed in the form of its pharmaceutically acceptable salts, in an anhydrous form or a hydrate or a solvate thereof. All such forms are useful within the scope of the present invention.

The term "efflux protein inhibitor" as used herein refers to any compound, a pharmaceutical or an excipient compound, that inhibits the action of any ABC transporter, e.g. those disclosed in Bakos et al. *Mol Pharmacol.*, 57, 760-768 (2002) and Maarten et al. *AIDS*, 16, 2295-2301 (2002).

In addition, it may be noted that an efflux protein inhibitor which enhances the bioavailability of a renin inhibitor may operate by one or more of a variety of mechanisms. That is, as is well known in the art, it may be a competitive or a non-competitive inhibitor, or it may operate by a mixed mechanism. Whether such an inhibitor can affect the efflux of a certain renin inhibitor depends, inter alia, upon the relative affinities of the renin inhibitor and the efflux protein inhibitor; the relative aqueous solubilities of the renin inhibitor and the efflux protein inhibitor, because this would affect the concentration of the two at the efflux pump in vivo when they are in competition; the absolute aqueous solubility of the efflux protein inhibitor, because it must achieve a sufficient concentration at the efflux pump in vivo to effectively inhibit the efflux; and the dose of the efflux protein inhibitor. For the purpose of this invention, an efflux protein inhibitor is any compound which improves the systemic exposure of a renin inhibitor, when the renin inhibitor is dosed orally or by any other route, and which is a substrate and/or an inhibitor of one or more of the drug efflux proteins/activities of intestinal epithelial cells or that in the hepatocytes.

As described herein above, the present invention provides a method for improving the bioavailability of a renin inhibitor, in particular, a δ-amino-γ-hydroxy-ω-aryl-alkanoic acid derivative, which method comprises co-administering a combination of a renin inhibitor and an efflux protein inhibitor.

Preferably, the efflux protein inhibitor of the present invention is a MDR1 inhibitor, e.g., PSC833.

Preferably, a δ-amino-γ-hydroxy-ω-aryl-alkanoic acid derivative of the present invention having the formula wherein $R_1$ is $C_{1-4}$alkoxy-$C_{1-4}$alkoxy or $C_{1-4}$alkoxy-$C_{1-4}$alkyl; $R_2$ is $C_{1-4}$alkyl or $C_{1-4}$alkoxy; and $R_3$ and $R_4$ are independently branched $C_{1-4}$alkyl; or a pharmaceutically acceptable salt thereof; is co-administered with a MDR1 inhibitor, e.g., PSC833.

More preferably, a δ-amino-γ-hydroxy-ω-aryl-alkanoic acid derivative of the present invention having formula (I) wherein $R_1$ is 3-methoxypropoxy; $R_2$ is methoxy; and $R_3$ and $R_4$ are isopropyl; or a pharmaceutically acceptable salt thereof; is co-administered with a MDR1 inhibitor, e.g., PSC833.

Most preferably, a δ-amino-γ-hydroxy-ω-aryl-alkanoic acid derivative of the present invention which is (2S,4S,5S,7S)-5-amino-4-hydroxy-2-isopropyl-7-[4-methoxy-3-(3-methoxy-propoxy)-benzyl]-8-methyl-nonanoic acid (2-carbamoyl-2-methyl-propyl)-amide hemifumarate, also known as SPP100, is co-administered with a MDR1 inhibitor, e.g., PSC833.

As disclosed herein above, a renin inhibitor, in particular, a δ-amino-γ-hydroxy-ω-aryl-alkanoic acid derivative, and efflux protein inhibitor may be co-administered as a pharmaceutical composition. The components may be administered together in any conventional dosage form, usually also together with a pharmaceutically acceptable carrier or diluent.

For oral administration the pharmaceutical composition comprising a renin inhibitor, in particular, a δ-amino-γ-hydroxy-ω-aryl-alkanoic acid derivative, and an efflux protein inhibitor can take the form of solutions, suspensions, tablets, pills, capsules, powders, microemulsions, unit dose packets and the like. Preferred are tablets and gelatin capsules comprising the active ingredient together with: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

More specifically, the present invention provides a pharmaceutical composition comprising a therapeutically effective amount of a renin inhibitor, preferably, a δ-amino-γ-hydroxy-ω-aryl-alkanoic acid derivative, in combination with an efflux protein inhibitor, said efflux protein inhibitor being present in an amount such that, following administration, the bioavailability of a renin inhibitor is improved by at least 5%.

Preferably, a pharmaceutical composition of the present invention comprises a MDR1 inhibitor, e.g., PSC833.

Preferably, a pharmaceutical composition of the present invention comprises a δ-amino-γ-hydroxy-ω-aryl-alkanoic acid derivative of the formula (I)

wherein $R_1$ is $C_{1-4}$alkoxy-$C_{1-4}$alkoxy or $C_{1-4}$alkoxy-$C_{1-4}$alkyl; $R_2$ is $C_{1-4}$alkyl or $C_{1-4}$alkoxy; and $R_3$ and $R_4$ are independently branched $C_{1-4}$alkyl; or a pharmaceutically acceptable salt thereof; in combination with a MDR1 inhibitor, e.g., PSC833.

More preferably, a pharmaceutical composition of the present invention comprises a δ-amino-γ-hydroxy-ω-aryl-alkanoic acid derivative of formula (i) wherein $R_1$ is 3-methoxypropoxy; $R_2$ is methoxy; and $R_3$ and $R_4$ are isopropyl; or a pharmaceutically acceptable salt thereof; in combination with a MDR1 inhibitor, e.g., PSC833.

Most preferably, a pharmaceutical composition of the present invention comprises (2S,4S,5S,7S)-5-amino-4-hydroxy-2-isopropyl-7-[4-methoxy-3-(3-methoxy-propoxy)-benzyl]-8-methyl-nonanoic acid (2-carbamoyl-2-methylpropyl)-amide hemifumarate in combination with a MDR1 inhibitor, e.g., PSC833.

Preferably, the bioavailability of a renin inhibitor, in particular, a δ-amino-γ-hydroxy-ω-aryl-alkanoic acid derivative, e.g., SPP100, or a pharmaceutically acceptable salt thereof, is improved by at least 5%.

Bioavailability of a drug may be assessed as known in the art by measuring AUCs, where AUC is the area under the curve (AUC) plotting the serum or plasma concentration of a drug along the ordinate (Y-axis) against time along the abscissa (X-axis). Generally, the values for AUC represent a number of values taken from all the subjects in a test population and are, therefore, mean values averaged over the entire test population.

Co-administration a renin inhibitor and an efflux protein inhibitor may also increase $C_{max}$ relative to dosing the renin inhibitor in the absence of an efflux protein inhibitor, and this is provided as a further aspect of the invention. $C_{max}$ is also well understood in the art as an abbreviation for the maximum drug concentration in serum or plasma of a test subject.

Since the present invention has an aspect that relates to treatment with a combination of compounds which may be co-administered separately, the invention also relates to combining separate pharmaceutical compositions in kit form. The kit comprises two separate pharmaceutical compositions: (1) a composition comprising a renin inhibitor, in particular, a δ-amino-γ-hydroxy-ω-aryl-alkanoic acid derivative, plus a pharmaceutically acceptable carrier or diluent; and (2) a composition comprising an efflux protein inhibitor, plus a pharmaceutically acceptable carrier or diluent. The amounts of (1) and (2) are such that, when co-administered separately, the bioavailability of a renin inhibitor, in particular, a δ-amino-γ-hydroxy-ω-aryl-alkanoic acid derivative, is improved by at least 5%. The kit comprises a container for containing the separate compositions such as a divided bottle or a divided foil packet, wherein each compartment contains a plurality of dosage forms (e.g., tablets) comprising (1) or (2). Alternatively, rather than separating the active ingredient-containing dosage forms, the kit may contain separate compartments each of which contains a whole dosage which in turn comprises separate dosage forms. An example of this type of kit is a blister-pack wherein each individual blister contains two (or more) tablets, one (or more) tablet(s) comprising a pharmaceutical composition (1), and the second (or more) tablet(s) comprising a pharmaceutical composition (2). Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician. In the case of the instant invention a kit therefore comprises:

(1) a therapeutically effective amount of a composition comprising a renin inhibitor, in particular, a δ-amino-γ-hydroxy-ω-aryl-alkanoic acid derivative, e.g., SPP100, or a pharmaceutically acceptable salt thereof, and a pharmaceutically acceptable carrier or diluent, in a first dosage form;

(2) a composition comprising an efflux protein inhibitor in an amount such that, following administration, the bioavailability of a renin inhibitor, in particular, a δ-amino-γ-hydroxy-ω-aryl-alkanoic acid derivative, e.g., SPP100, or a pharmaceutically acceptable salt thereof, is improved by at least 5%, and a pharmaceutically acceptable carrier or diluent, in a second dosage form; and (3) a container for containing said first and second dosage forms.

Ultimately, the present invention relates to a use of an efflux protein inhibitor, in particular, a MDR1 inhibitor, e.g., PSC833, for the manufacture of a medicament to improve the bioavailability, preferably oral bioavailability, of a renin inhibitor, preferably, a δ-amino-γ-hydroxy-ω-aryl-alkanoic acid derivative, e.g., SPP100, or a pharmaceutically acceptable salt thereof.

The efflux protein(s) involved in the drug efflux of a drug substance may be identified, and the corresponding kinetic parameters may be determined, i.e., Michaelis-Menten Constant and Maximal Drug Transport ($K_m$ and $J_{max}$) using methods known in the art, e.g., by an ATPase assay using Sf9 (Spodoptera fruigiperda) membrane vesicles expressing high levels of the selected ABC transporter. In this assay the ABC transporters remove substrates out of cells by using ATP hydrolysis as an energy source. ATP hydrolysis yields inorganic phosphate (Pi), which can be detected by a simple colorimetric reaction. The amount of Pi liberated by the transporter is proportional to the activity of the transporter. Membrane preparations containing ABC transporters show a baseline ATPase activity that varies for different transporters. Transported substrates increase this baseline ATPase activity, while inhibitors inhibit the baseline ATPase activity and/or the ATPase activity measured in the presence of a stimulating agent. Both, activation and inhibition studies may be performed. As illustrated herein in Example 1 (FIG. 1), SPP100 increases the ATPase activity in membrane vesicles expressing high levels of MDR1 with a $K_m$ value of about 3 µM, suggesting that the efflux system involved in SPP100 transport is possibly MDR1.

Figure 2:
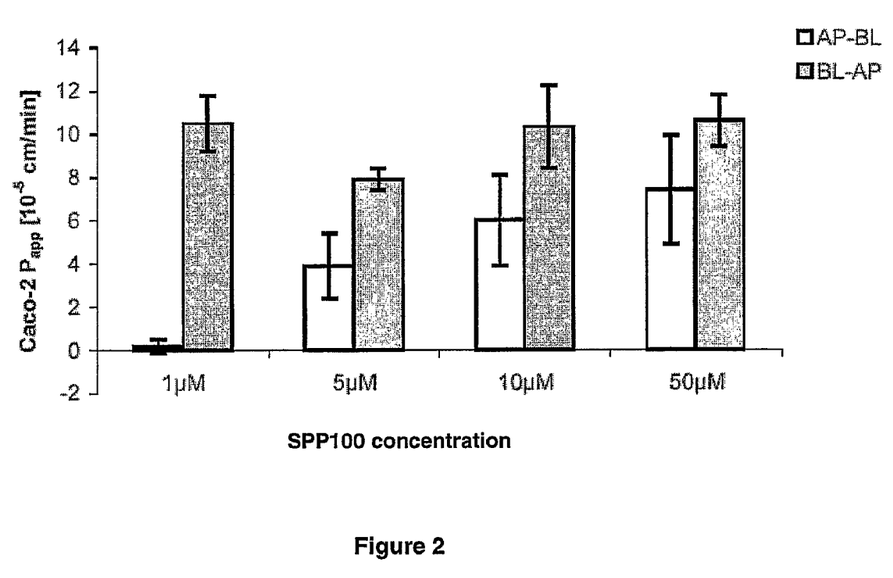
FIG. 2 shows bi-directional transport of the renin inhibitor SPP100 across Caco-2 cell monolayers in the apical (AP) to basolateral (BL) and BL-to-AP direction.
Figure 3:
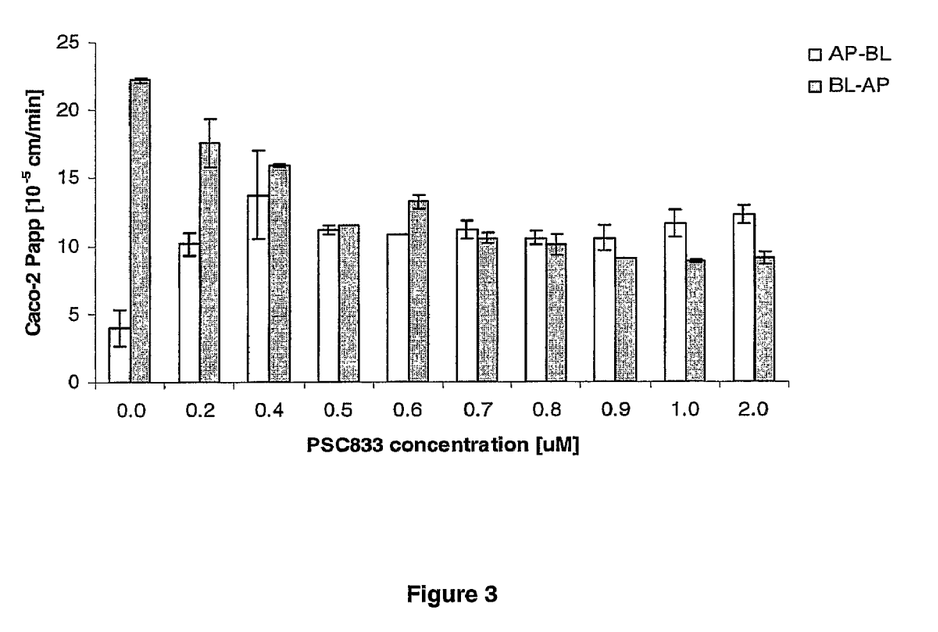
FIG. 3 shows the effect of the MDR1 inhibitor PSC833 on the permeability of the renin inhibitor SPP100 across Caco-2 cell monolayers.

Alternatively, the in vitro transporter affinity of a drug substance can be determined and approximated by a Caco-2 cell assay as described, e.g., in Camenisch et al., *Pharm. Act. Helv.* 71, 309-327 (1996), or as illustrated herein in the Examples. The identification of the transporter protein and the efficacy of a compound to inhibit the efflux system involved may as well be determined in the Caco-2 cell assay. For example, SPP100 is identified as a low to moderate permeable compound (intrinsic permeability <80%), being additionally a substrate for a prominent efflux system (FIG. 2). However, in the presence of the MDR1 inhibitor PSC833 the permeability of SPP100 increases significantly, i.e., PSC833 inhibits the efflux of SPP100 with an $IC_{50}$ value of about 0.1 µM (FIG. 3).

The effect in situ of co-administration of an efflux protein inhibitor, e.g., a MDR1 inhibitor, on the biliary excretion of a renin inhibitor may be investigated by comparing the amount of compound excreted into bile, in the presence and the absence of an efflux protein inhibitor.

Figure 4:
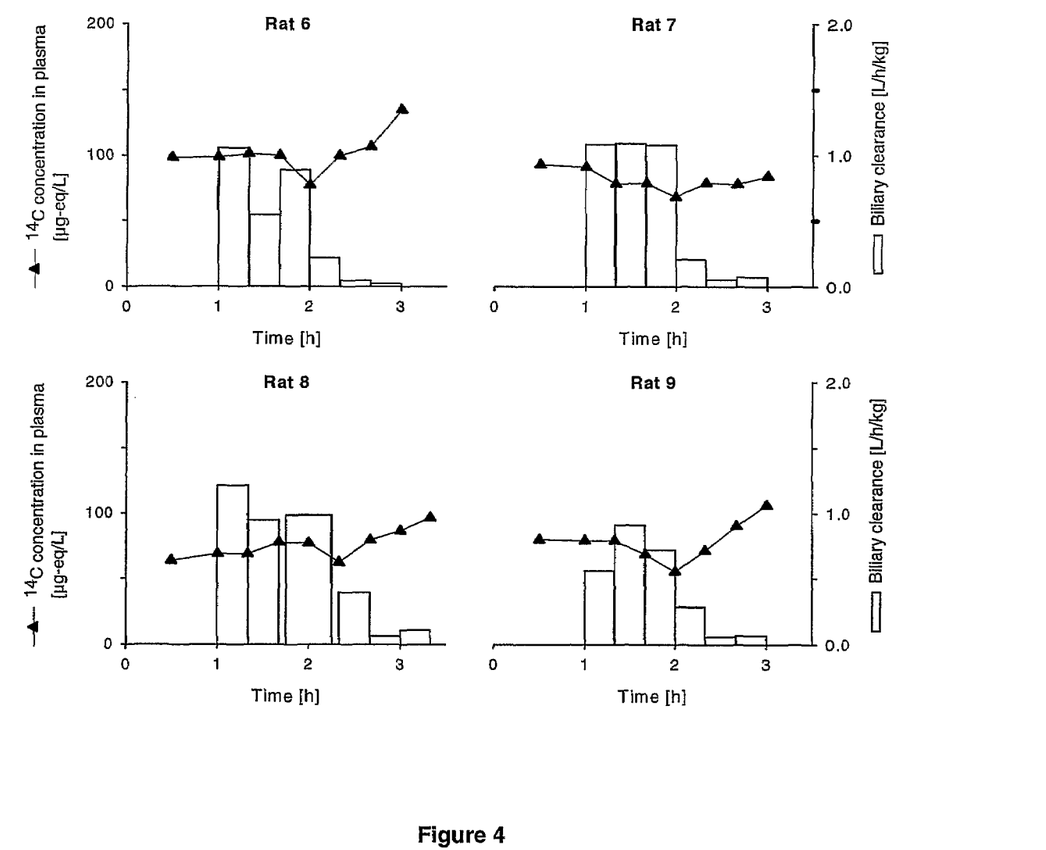
FIG. 4 shows the effect of the MDR1 inhibitor PSC833 on the concentration of the renin inhibitor SPP100 in plasma and on biliary clearance in rats during constant intravenous infusion.

For example, in the presence of PSC833 biliary clearance of SPP100 decreased by 97% as compared to control group (FIG. 4).

Similarly, the effect in vivo of co-administration of an efflux protein inhibitor, e.g., a MDR1 inhibitor, on the bioavailability of a renin inhibitor may be investigated by comparing the pharmacokinetic parameters, $C_{max}$ and AUCs, in the presence and the absence of an efflux protein inhibitor. As illustrated herein in Example 4 (FIG. 5) in orally dosed rats the dose-normalized AUC(0-$t_{last}$) of SPP100 increased in the presence of PSC833 about 70-fold compared to control group solely dosed with SPP100.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way.

EXAMPLE 1

ATPase Assay

Efflux mediated by the human MDR1, the human MRP1 or the human MRP2 is measured by incubating the purified membrane vesicles in the absence and the presence of a stimulating agent (Verapamil [40 µM] for MDR1, NEM-GS [10 mM] for MRP1 and Probenecid [1 mM] for MRP2) with different concentrations of a drug substance [0.046, 0.137, 0.41, 1.23, 3.7, 11.1, 33.3 and 100 µM] in transport buffer at pH 7.4 at 37° C.

A 5 mM stock solution of the therapeutic agent of interest will be prepared in a common organic solvent, e.g., dimethylsulfoxide, ethanol, methanol and acetonitrile, such a way that addition of the stock solution or its dilutions into assay mixture produces the above mentioned final concentrations, and the organic solvent used is 2% of the total volume (v/v). All the solutions used in this assay will be maintained at pH 7.4.

Membrane vesicles maintained at −80° C. will be used for the ATPase experiments. Transporter mediated efflux may be determined as described in literature (Sarkadi, B. Price, E. Boucher, R. Germann, U. and Scarborough, G. *J. Biol. Chem.* 1992, 267: 4854-4858). Briefly, membrane suspension in the presence and absence of a test drug, stimulating agent, $Na_3VO_4$ 60 mM and Glutathione 2 mM (only for MRP1 and MRP2 transporters) is pipetted into a 96-well plate and transferred to 37° C. for 5 min of preincubation. The ATPase reaction is started by addition of 25 mM Mg-ATP solution and subsequent incubation at 37° C. (20 min for MDR1, 60 min for MRP1 and 30 min for MRP2). Afterwards, the ATPase reaction is stopped by adding SDS (5%) to each incubation. After addition of ammonium molybdate/zinc acetate colorimetric detection reagent the plate is incubated for an addition 25 min at 37° C.

After incubating the OD is measured at 730 nm. Using a previously determined phosphate standard curve the Pi liberated [nmol/well] can be calculated. OD values will be presented as means ± standard deviations of the experiments performed (n=2). All statistical analyses are performed using Microsoft EXCEL 5.0c.

Figure 1:
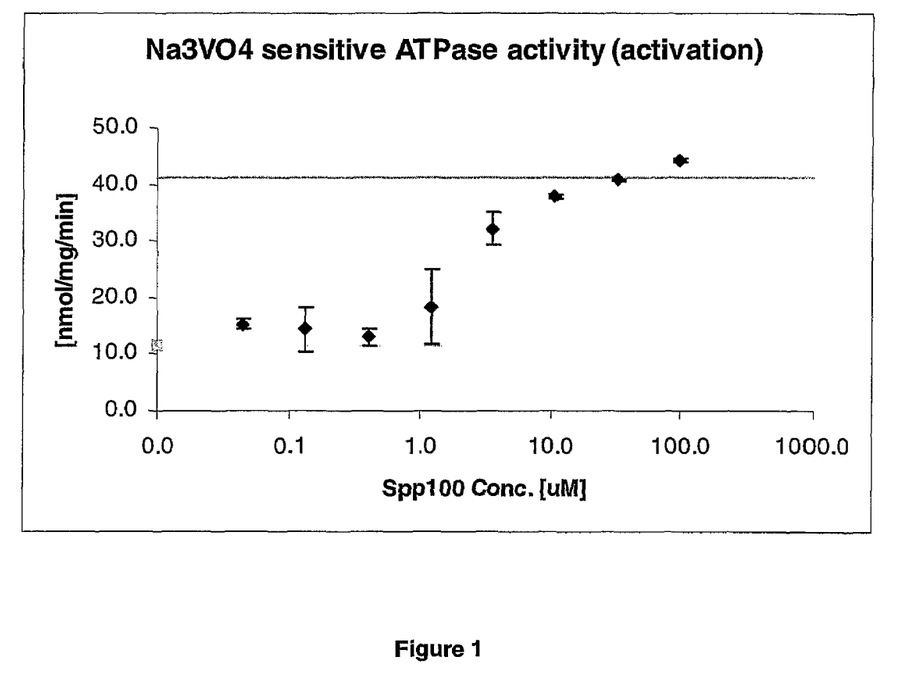
FIG. 1 shows the effect of the renin inhibitor SPP100 on the ATPase activity in membrane vesicles expressing high levels of MDR1.

To calculate the so-called specific ($Na_3VO_4$ sensitive) transporter ATPase activity for each drug and drug-concentration assayed the Pi values determined in the presence of $Na_3VO_4$ have to be subtracted from the Pi values measured without $Na_3VO_4$. The $Na_3VO_4$ sensitive transporter activity in terms of Pi liberated/mg membrane protein/min can be determined by dividing the numbers by the amount of membrane protein added to each well and the time of incubation in min (FIG. 1).

EXAMPLE 2

Caco-2 Cell Assay

Caco-2 cell monolayers grown on PET filters for 21-25 days are used for the transport experiments. The flux of compounds across Caco-2 cell monolayers grown on PET filters as well as across PET filters alone without Caco-2 cells is determined as follows: Prior to the transport experiment, the culture medium in the acceptor compartment (0.2 mL for apical and 1.0 mL for basolateral sides) is replaced with acceptor solution (HBSS, when relevant containing the inhibitor of interest) preincubated at 37° C. To start the experiment, the medium in the donor compartment (0.35 mL for apical and 1.15 mL for basolateral sides) is replaced with donor solution (compound in HBSS, when relevant containing inhibitor of interest) pre-incubated at 37° C. Aliquots of 150 µL are removed from the donor and the acceptor side after about 1 and 120 min. Transport experiments in both apical-to-basolateral and basolateral-to-apical directions are performed in triplicate at 37° C. in an incubator without shaking.

The suitability of Caco-2 cells for transport experiments is examined by measuring the permeability of [$^3$H]-mannitol at >0.1 µM and [$^3$H]-propranolol at >0.1 µM from apical to basolateral sides for 120 min in a total of 6 representative cell monolayers (3 for each compound) within the same batch of cells.

Radioactive samples are analyzed by liquid scintillation counting. All other non-radiolabeled samples are kept frozen at −20° C. until analysis by liquid chromatography/tandem mass spectrometry (LC-MS/MS).

Transport values of the compounds tested are determined using the following equation (Artursson et al., *Biochem. Biophys. Res. Comm.* 175: 880-885, 1991):

$$P_{app} = \frac{\Delta Q}{\Delta t \cdot A \cdot C_0}$$

where $P_{app}$ (cm/min) is the apparent permeability coefficient, $\Delta Q$ is the amount of compound found in the acceptor compartment at time t, $\Delta t$ (min) is the incubation time period, $C_0$ (μg/mL) is the initial concentration of the compound in the donor compartment and A (cm²) is the surface area of the membrane.

For labeled samples, the limit of quantitation (LOQ) is taken as the lowest sample concentration value obtained from the radioactive scale which is significantly higher than the measured blank value and for which the standard error of the measurement is lower than 20%. Under the conditions of this study, the LOQ of absolute radioactivity is 2 dpm for [$^{14}$C]-labeled SPP100 corresponding to 12 nmol/L.

$P_{app}$ values are presented as means ± standard deviations of the transport experiments performed (n=3). The statistical significance in differences between any two given data sets is examined by t-test. The probability level for assignment of significance of difference is p<0.025. All statistical analyses were performed using Microsoft EXCEL 5.0c.

For 1 μM concentration of SPP100 within a time period of 120 min an apical to basolateral transport of about $0.2 \cdot 10^{-5}$ cm/min is detectable. Basolateral to apical transport on the other side occurred with a permeability value of about $10 \cdot 10^{-5}$ cm/min, which is significantly higher than the apical to basolateral transport.

For 1, 5, 10 and 50 μM concentration of SPP100 a gradual increase of apical to basolateral transport is observed, approaching a plateau permeability value of about $7 \cdot 10^{-5}$ cm/min at 10 μM. Basolateral to apical transport on the other side does not change significantly with increasing concentrations.

The recovery values for Caco-2 transport of SPP100 (1, 5, 10 and 50 μM) are generally very high (<100%), indicating that SPP100 does not bind to the filter support or the plastic incubation environment.

Apical to basolateral flux for the paracellular marker Mannitol and the transcellular marker Propranolol are always below the threshold $P_{app}$ values of $3 \cdot 10^{-5}$ cm/min and $90 \cdot 10^{-5}$ cm/min, respectively. The determined apical to basolateral filter permeabilities are generally higher than the corresponding Caco-2 permeability data, indicating filter diffusion not to be the rate limiting step for Caco-2 transport (FIGS. 2 and 3).

EXAMPLE 3

In Situ Bile-Duct Cannulated Rat Experiment

The following study may be employed to elucidate the involvement of MDR1 and/or MRP2 in the biliary excretion of SPP100 in the rat. Therefore, the biliary clearance of SPP100 is assessed in male bile duct-cannulated and anaesthetized rats during a constant intravenous infusion of [$^{14}$C]-labeled SPP100 hemifumarate before and after the administration of PSC833 (a known inhibitor of MDR1 and MRP2) or probenecid (a known selective inhibitor of MRP2).

The animals that may be used are, e.g., male albino HAN: WIST rats, 4 to 5 animals in each treatment group.

[$^{14}$C]-labeled SPP100 hemifumarate is administered in 0.9% sodium chloride solution, and PSC833 and probenecid in a mixture of ethanol/polyethylene glycol 200/5% glucose solution in the ratio 1/3/1.

In all treatment groups, a constant concentration of the parent compound in plasma is achieved by bolus intravenous injection (2 mL/kg) of [$^{14}$C]-labeled SPP100 hemifumarate bolus solution (0.015 mg base/mL) with subsequent intravenous infusion (6.67 mL/h/kg) of [$^{14}$C]-labeled SPP100 hemifumarate infusion solution (0.022 mg base/mL).

Intravenous bolus administration of following compounds are carried out after two hours:

treatment group 1: a 1/3/1-mixture of ethanol/polyethylene glycol 200/5% glucose solution (5 mL/kg; vehicle);
treatment group 2: PSC833 with a dose of 10 mg/kg; and
treatment group 3: probenecid with a dose of 50 mg/kg.

For all treatment groups blood samples are collected at 0.5, 1, 1.33, 1.67, 2, 2.33, 2.67, 3 h after treatment and blood is immediately processed to plasma. Bile is collected for the time frame of 1 to 3 h in intervals of 20 min.

Detection Method:
for total radioactivity in all samples: LSC; LOQ 3.4 μg/L for plasma and bile; and
for detection of metabolite pattern in selected pools of samples: HPLC with radioactivity detection.

Following intravenous administration of the vehicle (ethanol/polyethylene glycol 200/5% glucose solution), no effect on the $^{14}$C concentration in plasma and on the biliary clearance of [$^{14}$C]-labeled compounds is detected during a constant infusion of [$^{14}$C]-labeled SPP100 hemifumarate to bile duct-cannulated rats.

Following PSC833 administration, the $^{14}$C concentration shows a trend towards a time dependent increase in plasma and a significant decrease in bile. The resulting biliary clearance of [$^{14}$C]-labeled compounds amounts to approximately 7% of the value obtained before PSC833 administration.

Following probenecid administration, no effect on the plasma concentrations of [$^{14}$C]-labeled compounds is observed in bile duct-cannulated rats. However, probenecid leads to an increase in bile flow (value after administration is about 65% higher than value prior administration) and to a decrease of the [$^{14}$C] concentration in bile (value is about 40% lower than the value prior to administration). Nevertheless, biliary clearance is similar in both time intervals (before and after probenecid administration).

From these results (FIG. 4) it may be concluded, that MDR1 seems to play an important role in the biliary clearance of SPP100 and SPP100-related compounds. Furthermore, MRP2 seems not to be involved in the biliary excretion of SPP100 and SPP100-related compounds.

EXAMPLE 4

In Vivo Bioavailability Experiment

The following study may be employed to investigate the relative oral bioavailability of SPP100 in male rats following a single oral administration of SPP100 hemifumarate with or without oral co-administration of PSC833. To elucidate a dose dependency of the co-administered PSC833, different doses of PSC833 (0, 5, 12.5, 25 and 50 mg/kg) are given at a defined dose of SPP100 hemifumarate (6 mg free base/kg).

The animals that may be used are, e.g., male albino HAN: WIST rats, 5 animals in each treatment group.

SPP100 hemifumarate is administered in 0.9% sodium chloride solution, and PSC833 in a mixture of ethanol/polyethylene glycol 200/5% glucose solution in the ratio 1/3/1 (vehicle).

First, the vehicle (5 mL/kg), and second SPP100 hemifumarate (2 mL/kg) are administered to the rats by gavage (time difference: 2-3 min). All rats receive SPP100 hemifumarate with a dose of 6 mg free base/kg. The following PSC833 doses are administered:

treatment group 1 and 6: a 1/3/1-mixture of ethanol/polyethylene glycol 200/5% glucose solution (5 mL/kg; vehicle);
treatment group 2: 50 mg/kg of PSC833;
treatment group 3: 25 mg/kg of PSC833;
treatment group 4: 12.5 mg/kg of PSC833; and
treatment group 5: 5 mg/kg of PSC833.

Blood samples are collected sublingually at 0.25, 0.5, 1, 2, 4, 8, 24 and 48 h after administration. Plasma is used for biochemical analysis.

Analytical Methods:

HPLC-MS/MS using APCI in SRM positive mode for SPP100, lowest LOQ in plasma ranges from 0.6 ng/mL to 0.7 ng/mL.

In rats orally dosed with SPP100 hemifumarate (6 mg base/kg) and vehicle, SPP100 is only detected in plasma up to 2 h post dosing. $C_{max}$ amounts to approximately 24.8±27 ng/mL and $t_{max}$ is reached at 0.44±0.1 h after dosing. The dose-normalized AUC(0-$t_{last}$) value is 2.38±3.4 [(ng*h/mL)/(mg/kg)].

Figure 5:
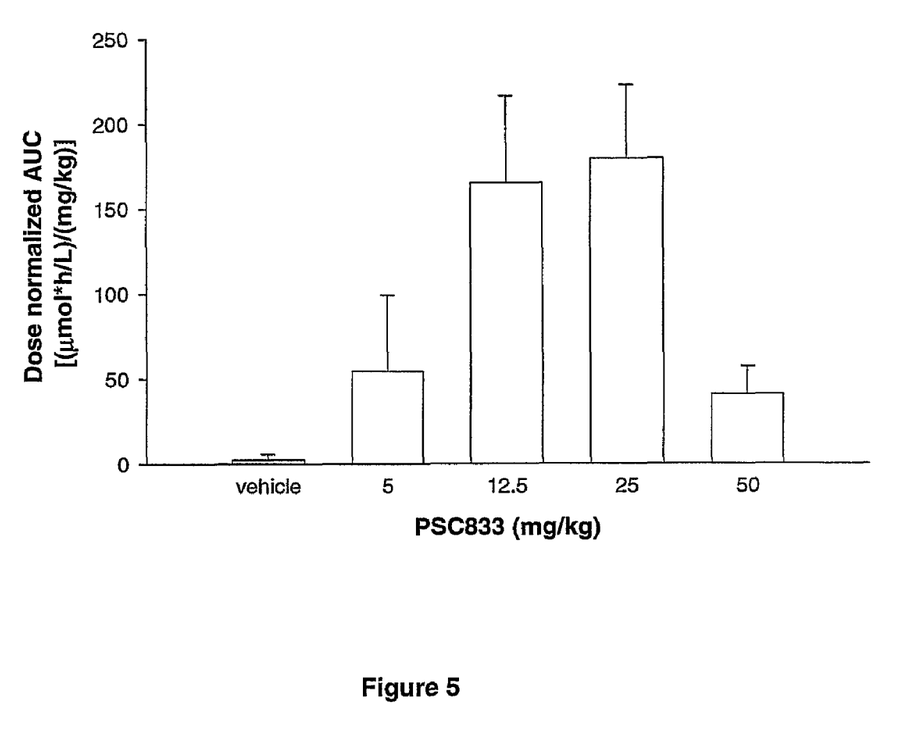
FIG. 5 shows dose-normalized area under the curve (AUC) values of the renin inhibitor SPP100 in the plasma of rats after single oral application in the absence and presence of PSC833.

In rats orally dosed with SPP100 hemifumarate (6 mg base/kg) and PSC833 (5, 12.5, 25 and 50 mg/dose), SPP100 is detected in plasma up to 24 or 48 h after dosing. Compared to the rats receiving the vehicle, $C_{max}$ increases to values of 35.7±18, 115±93, 81.4±19 and 26.7±18 ng/mL and $t_{max}$ to values of 4.8±1.8, 4.95±4.2, 15.2±18 and 3.06±1.9 h for PSC833 doses of 5, 12.5, 25 and 50 mg/kg, respectively. The dose-normalized AUC(0-$t_{last}$) values are about 23, 69, 76 and 17 times higher than in the vehicle group for co-administered PSC833 doses of 5, 12.5, 25 and 50 mg/kg, respectively. A reason for the relative low $f_{rel}$ value for the PSC833 dose of 50 mg/kg compared to the dose of 25 mg/kg could not be given (FIG. 5).

From these results it may be concluded, that at least one or both ABC efflux transporter proteins MDR1 and MRP2 seem to play an important role in the extent of the systemic exposure of SPP100 after oral administration.

EXAMPLE 5

(2S,4S,5S,7S)-5-Amino-4-hydroxy-2-isopropyl-7-[4-methoxy-3-(3-methoxy-propoxy)-benzyl]-8-methyl-nonanoic acid [$^{14}$C]-(2-carbamoyl-2-methyl-propyl)-amide, [$^{14}$C]-SPP100, hemifumarate A. Cyano-[$^{14}$C]-dimethyl-acetic acid methyl ester In an ampoule is placed a solution of sodium methoxide (119 mg; 2.2 mmol) in methanol (2 mL) at RT. Methyl cyanoacetate (99 mg, 1.0 mmol) is added at 0° C. The mixture is shaken for a few min at RT and then frozen to −192° C. under nitrogen and [$^{14}$C]-labeled methyl iodide (3.7 GBq at 2.04 GBq/mmol, 1.82 mmol, available from Amersham Biosciences), is vacuum transferred over to the reaction mixture. The ampoule is sealed under vacuum and allowed to warm slowly to RT over a period of 1 h. The ampoule is vibrated at 50° C. for 16 h. The ampoule is then re-frozen to −192° C. and the volatile solvent and unreacted [$^{14}$C]-methyl iodide are removed by lyophilization. The crude cyano-[$^{14}$C]-dimethyl-acetic acid methyl ester is then analyzed by GC to ensure that <0.2% mono-methylated by-product is formed. The material is then used for the next step without further purification.

B. 2-Cyano-2,2-[$^{14}$C]-dimethyl-acetamide

Ammonia gas is bubbled into a flask containing dry methanol for 30 min at RT or until the molarity is 5 M or above. To crude title A compound, cyano-[$^{14}$C]-dimethylacetic acid methyl ester, is added the freshly prepared 5.5 M $NH_3$ in MeOH (3 mL, 16.5 mmol) at RT. The reaction is stirred at RT for 2 h after which all of the starting material is converted to the nitrile product as evidenced by GC analysis according to the following method: 10 min at 70° C., then incrementing temperature by 10° C./min to 200° C., then staying at 200° C. for 10 min. Following completion of the reaction the solvent is removed by lyophilization and the product is purified by flash chromatography (ethyl acetate→ethylacetate/10% methanol) to give 2.813 GBq of 2-cyano-2,2-[$^{14}$C]-dimethyl-acetamide.

C. 3-Amino-2,2-[$^{14}$C]-dimethyl-propionamide

To freshly purified title B compound, 2-cyano-2,2-[$^{14}$C]-dimethyl-acetamide (2.813 GBq, 77 mg, 0.69 mmol) is added a freshly prepared 5.5 M solution of $NH_3$ in MeOH at RT followed by 5% $Rh/Al_2O_3$ (33 mg). The reaction is stirred at 55° C. for up to 5 h and monitored by GC every 1 h until all of the starting material is converted to product. GC method: 1 min at 80° C., then incremented by 20° C./min to 240° C. followed by 1 min at 240° C. Following completion of the reaction, the mixture is filtered through Celite (Hyflo), the solvent is removed on a rotary evaporator and the product is purified by flash chromatography ($CH_2Cl_2$/2% MeOH/$NH_3$→$CH_2Cl_2$/5% MeOH/$NH_3$→$CH_2Cl_2$/10% MeOH/$NH_3$) to give 2.7 GBq of 3-amino-[$^{14}$C]2,2-dimethyl-propionamide as a white solid. This product may be stored as solid for periods of longer than 1 week. For long term storage, 3-amino-2,2-[$^{14}$C]-dimethyl-propionamide may be dissolved in EtOH/20% toluene at −80° C. at a concentration no greater than 50 MBq/mL.

D. (2S,4S,5S,7S)-5-Amino-4-hydroxy-2-isopropyl-7-[4-methoxy-3-(3-methoxy-propoxy)-benzyl]-8-methyl-nonanoic acid [$^{14}$C]-(2-carbamoyl-2-methyl-propyl)-amide, [$^{14}$C]-SPP100, hemifumarate The title C compound, 3-amino-2,2-[$^{14}$C]-dimethyl-propionamide may be employed for the preparation of the title D compound, [$^{14}$C]-labeled SPP100 hemifumarate, according to methods known in the art, e.g., as described in U.S. Pat. No. 6,730,798.

What is claimed is:

1. A method of improving the bioavailability of a renin inhibitor, which method comprises co-administering, to a mammal in need such treatment, a combination of a renin inhibitor and an efflux protein inhibitor, wherein the efflux protein inhibitor is PSC833 and the renin inhibitor is a σ-amino-γ-hydroxy-ω-aryl-alkanoic acid amide derivative represented by the formula wherein $R_1$ is $C_{1-4}$ alkoxy-$C_{1-4}$ alkoxy or $C_{1-4}$ alkoxy-$C_{1-4}$ alkyl: $R_2$ is $C_{1-4}$ alkyl or $C_{1-4}$ alkoxy; and $R_3$ and $R_4$ are independently branched $C_{1-4}$ alkyl; or a pharmaceutically acceptable salt thereof.

2. A method according to claim 1, wherein $R_1$ is 3-methoxypropoxy; $R_2$ is methoxy; and $R_3$ and $R_4$ are isopropyl; or a pharmaceutically acceptable salt thereof.

3. A method according to claim 2, wherein the σ-amino-γ-hydroxy-ω-aryl-alkanoic acid amide derivative is (2S,4S,5S,7S)-5-amino-4-hydroxy-2-isopropyl-7-[4-methoxy-3-(3-methoxy-propoxy)-benzyl]-8-methyl-nonanoic acid (2-carbamoyl-2-methyl-propyl)-amide hemifumarate.

4. A pharmaceutical composition comprising a therapeutically effective amount of a renin inhibitor in combination with an efflux protein inhibitor, said efflux protein inhibitor being present in an amount such that, following administration, the bioavailability of a renin inhibitor is improved by at least 5%, wherein the efflux protein inhibitor is PSC833 and the renin inhibitor is a σ-amino-γ-hydroxy-ω-aryl-alkanoic acid amide derivative represented by the formula wherein $R_1$ is $C_{1-4}$ alkoxy-$C_{1-4}$ alkoxy or $C_{1-4}$ alkoxy-$C_{1-4}$ alkyl: $R_2$ is $C_{1-4}$ alkyl or $C_{1-4}$ alkoxy; and $R_3$ and $R_4$ are independently branched $C_{1-4}$ alkyl; or a pharmaceutically acceptable salt thereof.

5. A pharmaceutical composition according to claim 4, wherein the σ-amino-γ-hydroxy-ω-aryl-alkanoic acid amide derivative is a compound of formula (I) wherein $R_1$ is 3-methoxypropoxy; $R_2$ is methoxy; and $R_3$ and R4 are isopropyl; or a pharmaceutically acceptable salt thereof.

6. A pharmaceutical composition according to claim 5, wherein σ-amino-γ-hydroxy-ω-aryl-alkanoic acid amide derivative is (2S,4S,5S,7S)-5-amino-4-hydroxy-2-isopropyl-7-[4-methoxy-3-(3-methoxy-propoxy)-benzyl]-8-methyl-nonanoic acid (2-carbamoyl-2-methyl-propyl)-amide hemifumarate.

* * * * *